(12) United States Patent
Kasahara et al.

(10) Patent No.: US 11,197,652 B2
(45) Date of Patent: Dec. 14, 2021

(54) RADIOGRAPHIC IMAGE ANALYSIS APPARATUS AND RADIOGRAPHIC IMAGE ANALYSIS SYSTEM

(71) Applicant: KONICA MINOLTA, INC., Tokyo (JP)

(72) Inventors: Kazuo Kasahara, Kanazawa (JP); Isao Matsumoto, Kanazawa (JP); Rie Tanaka, Kanazawa (JP); Masaya Tamura, Kanazawa (JP); Noriyuki Ohkura, Kanazawa (JP); Junsei Horii, Kanazawa (JP); Shintaro Muraoka, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 167 days.

(21) Appl. No.: 16/391,025

(22) Filed: Apr. 22, 2019

(65) Prior Publication Data

US 2019/0328346 A1 Oct. 31, 2019

(30) Foreign Application Priority Data

Apr. 26, 2018 (JP) .............................. JP2018-084693

(51) Int. Cl.
*A61B 6/00* (2006.01)
*A61B 5/00* (2006.01)
(Continued)

(52) U.S. Cl.
CPC ................ *A61B 6/50* (2013.01); *A61B 5/004* (2013.01); *A61B 6/5217* (2013.01);
(Continued)

(58) Field of Classification Search
CPC ......... A61B 6/50; A61B 5/004; A61B 6/5217; A61B 5/08; A61B 5/6889; A61B 6/463;
(Continued)

(56) References Cited

U.S. PATENT DOCUMENTS 6,175,755 B1 * 1/2001 Hogg ........................ G06T 7/62
600/407
8,553,955 B2 * 10/2013 Arakita ................. G06T 7/0016
382/128

(Continued)

FOREIGN PATENT DOCUMENTS

JP 2009153678 A 7/2009
JP 2016526466 A 9/2016

(Continued)

OTHER PUBLICATIONS

Japanese Office Action (and English language translation thereof) dated Oct. 5, 2021, issued in Japanese Application No. 2018-084693.

*Primary Examiner* — Michael S Osinski
(74) *Attorney, Agent, or Firm* — Holtz, Holtz & Volek PC

(57) ABSTRACT

A radiographic image analysis apparatus includes a hardware processor that calculates an area of a lung field from a chest image obtained by radiation imaging of a chest in one direction, and estimates a residual volume, a functional residual capacity, a total lung capacity or a residual volume ratio of the lung field, based on the calculated lung field area.

19 Claims, 9 Drawing Sheets

(51) Int. Cl.
*G06T 7/00* (2017.01)
*A61B 5/08* (2006.01)
(52) U.S. Cl.
CPC .............. *G06T 7/0012* (2013.01); *A61B 5/08* (2013.01); *G06T 2207/10116* (2013.01); *G06T 2207/30061* (2013.01)
(58) Field of Classification Search
CPC ....... A61B 6/486; A61B 6/032; A61B 6/5235; A61B 5/091; A61B 5/055; A61B 5/087; A61B 2017/00809; G06T 7/0012; G06T 2207/30061; G06T 2207/10116; G06T 7/62; G06T 2207/10081; G06T 2207/10072; G06T 2207/10088; G16H 50/30

See application file for complete search history.

(56) References Cited

U.S. PATENT DOCUMENTS

| | | | | |
|---|---|---|---|---|
| 9,064,302 | B2* | 6/2015 | Muraoka | G06K 9/3241 |
| 9,117,287 | B2* | 8/2015 | Masumoto | A61B 6/032 |
| 9,125,621 | B2* | 9/2015 | Nagatsuka | A61B 6/463 |
| 9,198,628 | B2* | 12/2015 | Shimada | A61B 6/4405 |
| 9,237,877 | B2* | 1/2016 | Noji | A61B 5/0205 |
| 9,730,666 | B2* | 8/2017 | Yamagata | A61B 6/5235 |
| 10,702,192 | B2 | 7/2020 | Nakazawa et al. | |
| 2004/0109595 | A1* | 6/2004 | Luo | G06T 7/149 |
| | | | | 382/132 |
| 2005/0147285 | A1* | 7/2005 | Tago | G06T 7/254 |
| | | | | 382/130 |
| 2012/0055476 | A1* | 3/2012 | Choncholas | A61M 16/0051 |
| | | | | 128/204.22 |
| 2012/0072193 | A1* | 3/2012 | De Backer | A61M 16/021 |
| | | | | 703/2 |
| 2012/0215504 | A1* | 8/2012 | Parker | A61B 5/0813 |
| | | | | 703/2 |
| 2012/0244169 | A1* | 9/2012 | Lipson | A61P 9/00 |
| | | | | 424/158.1 |
| 2013/0338489 | A1* | 12/2013 | Prisk | A61B 5/055 |
| | | | | 600/420 |
| 2014/0336499 | A1* | 11/2014 | Fenchel | A61B 6/037 |
| | | | | 600/411 |
| 2015/0031979 | A1* | 1/2015 | Rappaport | A61B 5/7278 |
| | | | | 600/407 |
| 2015/0042677 | A1* | 2/2015 | Shimamura | A61B 6/461 |
| | | | | 345/632 |
| 2015/0238270 | A1* | 8/2015 | Raffy | G16H 30/40 |
| | | | | 600/407 |
| 2015/0289785 | A1* | 10/2015 | Bojovic | A61M 16/0069 |
| | | | | 600/534 |
| 2016/0106341 | A1 | 4/2016 | Adam et al. | |
| 2016/0128782 | A1* | 5/2016 | Wei | A61B 5/091 |
| | | | | 382/131 |
| 2016/0210739 | A1* | 7/2016 | Maack | G06T 7/68 |
| 2016/0345861 | A1* | 12/2016 | Nielsen | A61B 5/0813 |
| 2017/0236275 | A1* | 8/2017 | Jung | A61B 5/0062 |
| | | | | 382/131 |
| 2017/0323432 | A1* | 11/2017 | Funabasama | A61B 6/463 |
| 2018/0055414 | A1* | 3/2018 | Bieri | A61B 5/055 |
| 2018/0161102 | A1* | 6/2018 | Wei | G06T 7/62 |
| 2019/0328276 | A1* | 10/2019 | Woo | A61B 5/091 |
| 2020/0051240 | A1* | 2/2020 | Chassagnon | G06T 7/62 |
| 2020/0379636 | A1* | 12/2020 | Takasawa | G06F 3/0488 |
| 2021/0052228 | A1* | 2/2021 | Abe | A61B 6/00 |

FOREIGN PATENT DOCUMENTS

| | | |
|---|---|---|
| JP | 2017176828 A | 10/2017 |
| JP | 2018000281 A | 1/2018 |

* cited by examiner

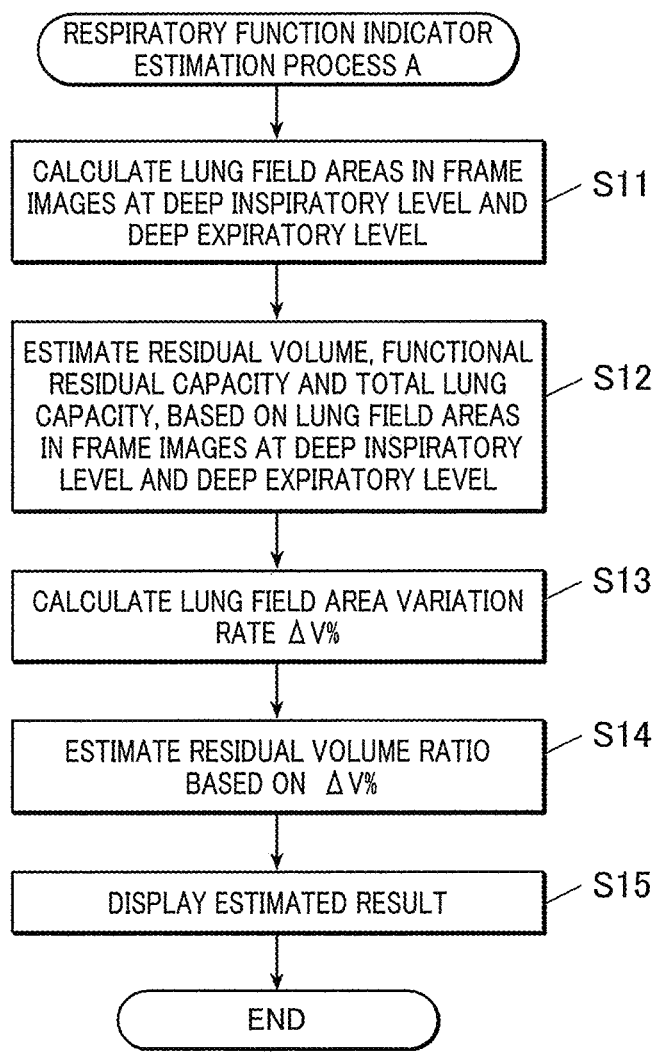

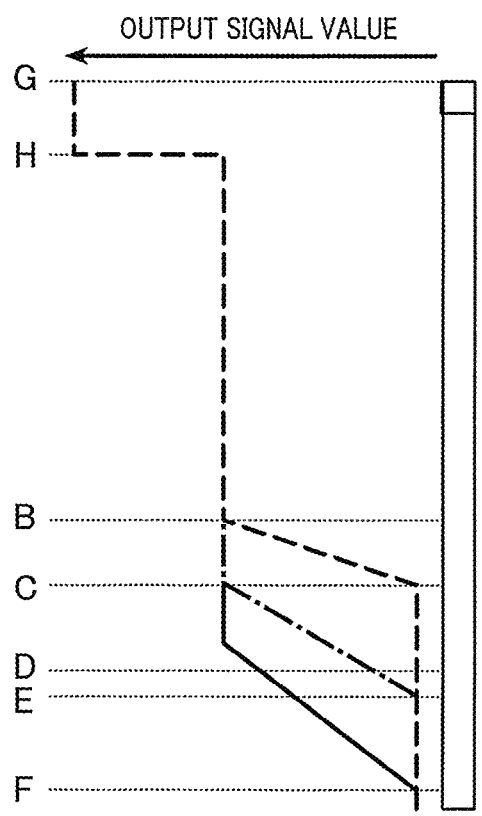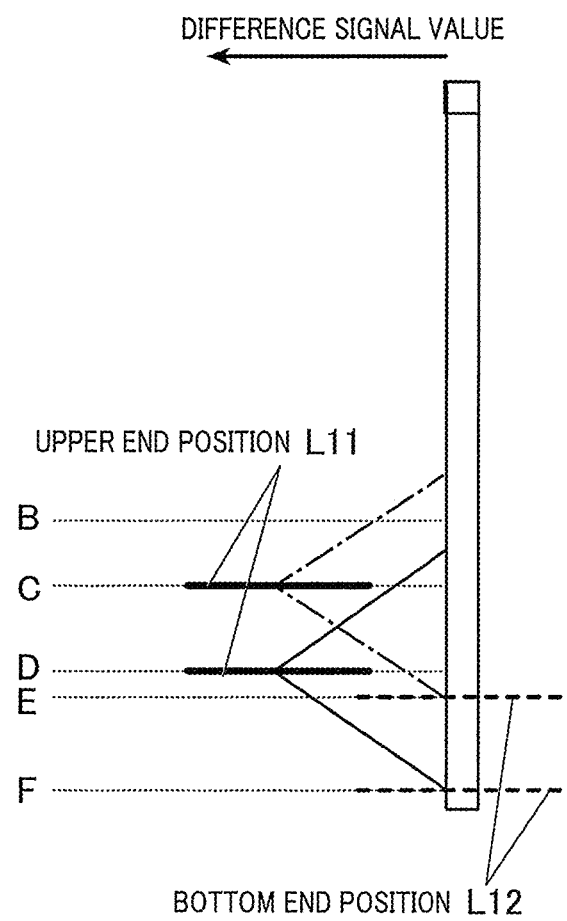

RADIOGRAPHIC IMAGE ANALYSIS APPARATUS AND RADIOGRAPHIC IMAGE ANALYSIS SYSTEM

BACKGROUND

Technological Field

The present invention relates to a radiographic image analysis apparatus and a radiographic image analysis system.

Description of the Related Art

Indicators related to the respiratory function, such as the residual volume, functional residual capacity, total lung capacity, and the residual volume ratio (residual volume/total lung capacity) calculable therefrom, (called respiratory function indicators) are information useful for diagnosing pulmonary diseases, such as COPD. However, the information cannot be easily measured by spirometry and is, typically, measured by any of methods including the helium closed circuit method, denitrogenation open circuit method, and body plethysmographic method. However, a medical instrument capable of such measurement is typically expensive and large in size. In particular, it is difficult for small medical facilities, such as clinics and small hospitals, to measure the residual volume, functional residual capacity, and total lung capacity. A method of easily measuring such indicators has been awaited.

It is also very important to identify the state of dynamic pulmonary hyperinflation in view of identifying the cause of shortness of breath in a COPD patient. The dynamic pulmonary hyperinflation is identified even in an early stage of COPD, and is effective information for early diagnosis accordingly. A method of easily measuring an indicator indicating the state of dynamic pulmonary hyperinflation has been awaited.

For example, Patent Literature 1 (Japanese Patent Laid-Open No. 2009-153678) describes a method of calculating estimated ventilations at the phases of the maximal expiratory level and the maximal inspiratory level on the basis of the ventilations (vital capacity or tidal volume) from the maximal expiratory level to the maximal inspiratory level measured by spirometry or the like and of the total signal value amount of variation in signal values in a lung field region in chest dynamic images varying between the maximal inspiratory level and the maximal expiratory level.

However, the technique described in Patent Literature 1 is nothing other than a method of estimating information measurable by spirometry from images, but does not describe, at all, a method of estimating respiratory function indicators, such as the residual volume, functional residual capacity, total lung capacity, and residual volume ratio.

SUMMARY

The present invention has an object to allow respiratory function indicators to be easily obtained; the indicators include the residual volume, functional residual capacity, total lung capacity, and residual volume ratio.

To achieve the object described above, a radiographic image analysis apparatus in which an aspect of the present invention is reflected includes a hardware processor that calculates an area of a lung field from a chest image obtained by radiation imaging of a chest in one direction, and estimates a residual volume, a functional residual capacity, a total lung capacity or a residual volume ratio of the lung field, based on the calculated lung field area.

A radiographic image analysis system where an aspect of the present invention is reflected includes:

a radiographic imaging apparatus that performs radiation imaging of a chest, and obtains a chest image; and the radiographic image analysis apparatus.

BRIEF DESCRIPTION OF THE DRAWINGS

The aforementioned object, advantageous effects and characteristics will be fully comprehended with reference to the following detailed description and the accompanying drawings. Note that these do not intend to limit the present invention. Here, the advantages and features provided by one or more embodiments of the invention will become more fully understood from the detailed description given hereinbelow and the appended drawings which are given by way of illustration only, and thus are not intended as a definition of the limits of the present invention.

FIG. 3 is a flowchart showing a respiratory function indicator estimation process A executed by a controller of a diagnostic console in FIG. 1 in a first embodiment;

FIG. 9A schematically shows the output signal value on line A-A' in the three front chest images shown in FIG. 8;

FIG. 9B schematically shows a difference signal value;

DETAILED DESCRIPTION OF EMBODIMENTS

Hereinafter, one or more embodiment of the present invention will be described with reference to the drawings. However, the scope of the invention is not limited to the disclosed embodiments. Note that the scope of the invention is not limited to the illustrated examples.

First Embodiment

[Configuration of Radiographic Image Analysis System 100]

First, the configuration of a first embodiment of the present invention is described.

Figure 1:
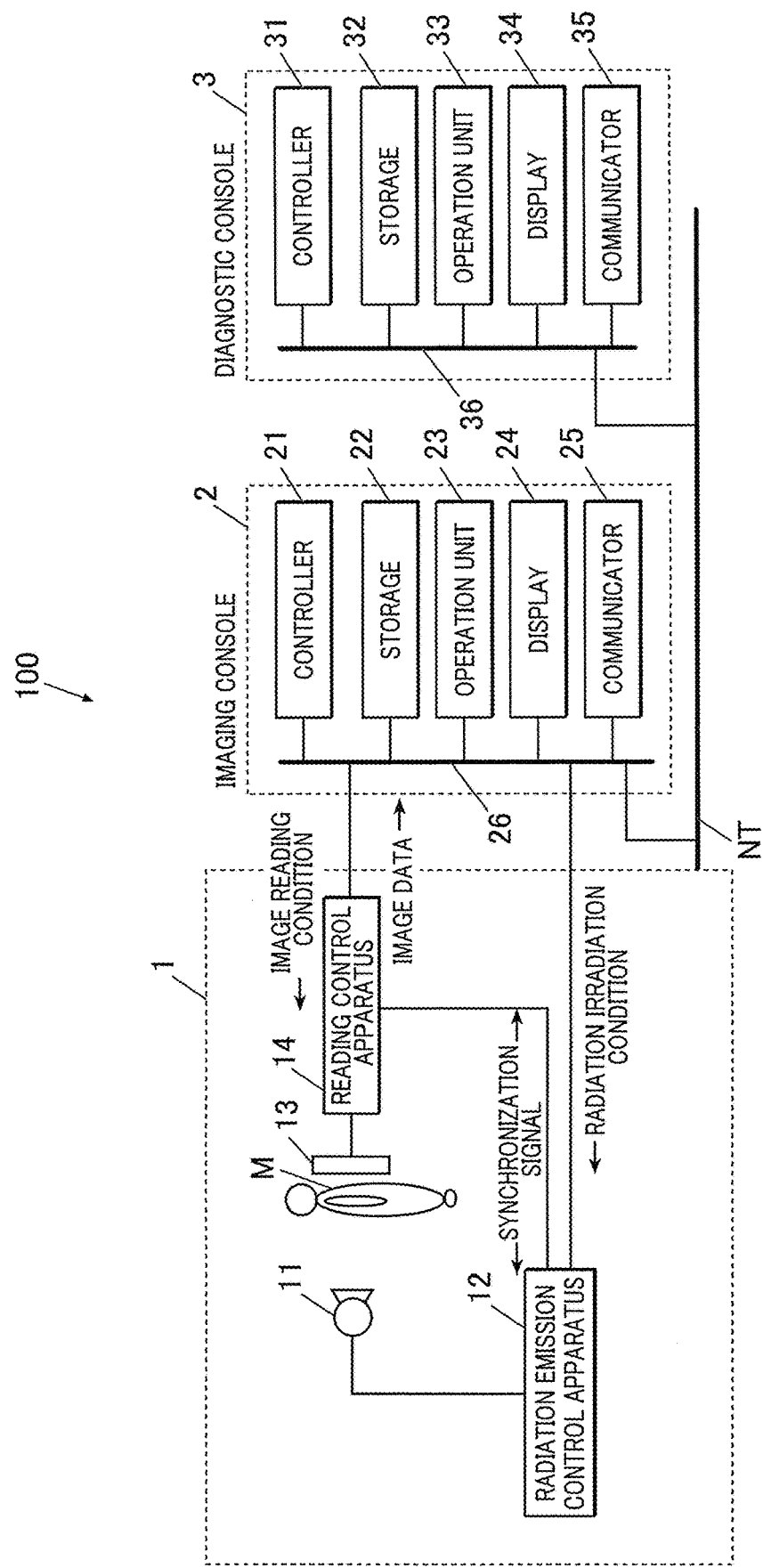
FIG. 1 shows the entire configuration of a radiographic image analysis system according to an embodiment of the present invention.

FIG. 1 shows the entire configuration of a radiographic image analysis system 100 according to this embodiment.

As shown in FIG. 1, in the radiographic image analysis system 100, an imaging apparatus 1 and an imaging console 2 are connected to each other by a communication cable or the like, and the imaging console 2 and a diagnostic console 3 are connected to each other via a communication network NT, such as a LAN (Local Area Network). The apparatuses constituting the radiographic image analysis system 100 conforms to the DICOM (Digital Image and Communications in Medicine) standard. Communication between the apparatuses is performed in conformity with DICOM.

[Configuration of Imaging Apparatus 1]

The imaging apparatus 1 is an imager that images the dynamics of an imaging object having a cycle, such as a change of form due to inflation and contraction of lungs accompanying respiratory motion, and heartbeats, for example. The dynamic imaging is to obtain multiple images representing the dynamics of an imaging object by generating pulsed radiation, such as X-rays, and repetitively irradiating the imaging object with the radiation (pulsed irradiation) at predetermined intervals, or by generating radiation with a low dose rate and irradiating the object uninterruptedly and continuously (continuous irradiation). A series of images obtained by dynamic imaging is called a dynamic image. Each of the images constituting the dynamic image is called a frame image. In the following embodiment, a case of dynamically imaging a front chest through pulsed irradiation is exemplified and described.

A radiation source 11 is disposed at a position opposite to a radiation detector 13, with an imaging object M (the chest of a subject) intervening therebetween, and irradiates the imaging object M with radiation (X-rays) in a state where no contrast agent is administered, according to the control by a radiation emission control apparatus 12.

The radiation emission control apparatus 12 is connected to the imaging console 2, and controls the radiation source 11 to perform radiation imaging on the basis of a radiation irradiation condition input through the imaging console 2. The radiation irradiation condition input through the imaging console 2 includes, for example, the pulse rate, the pulse width, the pulse interval, the number of imaging frames per imaging time, the value of X-ray tube current, the value of X-ray tube voltage and an added filter type. The pulse rate is the number of irradiations with radiation per second, and coincides with the frame rate described later. The pulse width is a time period of irradiation with radiation per radiation irradiation. The pulse interval is a time period from the start of one irradiation with radiation to the start of the next irradiation with radiation, and coincides with the frame interval described later.

The radiation detector 13 includes a semiconductor image sensor, such as FPD (Flat Panel Detector). The FPD includes, for example, a glass substrate and the like. Multiple detection elements (pixels) are arranged at predetermined positions on the substrate in a matrix manner. The detection elements each detect radiation having been emitted from the radiation source 11 and passed through at least the imaging object M according to the intensity, convert the detected radiation into an electric signal and accumulate the signal. Each pixel includes a switcher, such as TFT (Thin Film Transistor), for example. FPDs include an indirect type that converts X-rays into an electric signal by a photoelectric conversion element through a scintillator, and a direct type that directly converts X-rays into an electric signal. Any of the types may be adopted.

The radiation detector 13 is held by an imaging base 15 (see FIGS. 10A to 10C), and is provided so as to face the radiation source 11, with the imaging object M intervening therebetween.

A reading control apparatus 14 is connected to the imaging console 2. The reading control apparatus 14 controls the switcher of each pixel of the radiation detector 13 to switch reading of the electric signal accumulated in this pixel on the basis of an image reading condition input through the imaging console 2, and reads the electric signal accumulated in the radiation detector 13, thus obtaining image data. This image data is a frame image. The reading control apparatus 14 outputs the obtained frame image to the imaging console 2. The image reading condition includes, for example, the frame rate, frame interval, pixel size, and image size (matrix size). The frame rate is the number of frame images obtained per second, and coincides with the pulse rate. The frame interval is a time period from the start of one time of an operation of obtaining the frame image to the start of the operation of obtaining the next frame image, and coincides with the pulse interval.

Here, the radiation emission control apparatus 12 and the reading control apparatus 14 are connected to each other, and mutually exchange synchronization signals to synchronize a radiation irradiation operation and an image reading operation with each other.

[Configuration of Imaging Console 2]

The imaging console 2 outputs the radiation irradiation condition and the image reading condition to the imaging apparatus 1, controls the imaging apparatus 1 to perform the radiation imaging and the operation of reading a radiographic image, and displays the dynamic image obtained by the imaging apparatus 1 for verifying whether or not the image is an image suitable for verifying positioning by an imaging practitioner, such as an imaging technician, and for diagnosis.

As shown in FIG. 1, the imaging console 2 includes a controller 21, a storage 22, an operation unit 23, a display 24, and a communicator 25. These components are connected to each other via a bus 26.

The controller 21 includes a CPU (Central Processing Unit) and an RAM (Random Access Memory). The CPU of the controller 21 reads a system program and various processing programs stored in the storage 22 and deploys the programs in the RAM according to an operation through the operation unit 23, executes various processes including an imaging control process, described later, according to the deployed program, and controls the operation of each component of the imaging console 2 and the radiation irradiation operation and the reading operation of the imaging apparatus 1 in a centralized manner.

The storage 22 includes a nonvolatile semiconductor memory, or a hard disk. The storage 22 stores various programs to be executed by the controller 21, and parameters required to execute the processes by the programs, or data including processing results. For example, the storage 22 stores programs for executing the imaging control process shown in FIG. 2. The storage 22 stores the radiation irradiation condition and the image reading condition in association with an imaging object site (here, assumed as a chest). The various programs are stored in a form of computer-readable program codes. The controller 21 sequentially executes operations according to the program codes.

The operation unit 23 includes a keyboard provided with cursor keys, numeric input keys and various function keys, and a pointing device, such as a mouse, and outputs, to the controller 21, an instruction signal input through a key operation into the keyboard or a mouse operation. The operation unit 23 may include a touch panel on a display screen of the display 24. In this case, the operation unit 23 outputs, to the controller 21, the instruction signal input through the touch panel.

The display 24 may be a monitor, such as an LCD (Liquid Crystal Display) or a CRT (Cathode Ray Tube), and displays an input instruction, data and the like from the operation unit 23, according to an instruction of a display signal input from the controller 21.

The communicator 25 includes an LAN adaptor, and a modem or a TA (Terminal Adapter), and controls data transmission and reception to and from each apparatus connected to the communication network NT.

[Configuration of Diagnostic Console 3]

The diagnostic console 3 is a radiographic image analysis apparatus for obtaining the dynamic image from the imaging console 2, and displaying the obtained dynamic image and an analysis result of the dynamic image to support a doctor's diagnosis.

As shown in FIG. 1, the diagnostic console 3 includes a controller 31, a storage 32, an operation unit 33, a display 34, and a communicator 35. These components are connected to each other via a bus 36.

The controller 31 includes a CPU and a RAM. The CPU of the controller 31 reads a system program and various processing programs stored in the storage 32 and deploys the programs in the RAM according to an operation through the operation unit 33, executes various processes including a respiratory function indicator estimation process A, described later, according to the deployed program, and controls the operation of each component of the diagnostic console 3 in a centralized manner.

The storage 32 includes a nonvolatile semiconductor memory, or a hard disk. The storage 32 stores various programs including a program for executing the respiratory function indicator estimation process A in the controller 31, and parameters required to execute the processes by the programs, or data including processing results. These various programs are stored in a form of computer-readable program codes. The controller 31 sequentially executes operations according to the program codes.

The storage 32 stores the taken dynamic image in association with patient information (e.g., patient ID, patient name, height, weight, age, gender, etc.), examination information (e.g., examination ID, examination date, imaging object site (chest in this case), imaging direction (front, side), etc.).

The storage 32 stores a calculation expression for calculating the estimates of the residual volume, the functional residual capacity and the total lung capacity from the lung field area calculated from the front chest image, or a table representing the correspondence relationship between the lung field area calculated from the front chest image, the residual volume, the functional residual capacity and the total lung capacity, or a calculation expression for calculating the estimate of the residual volume ratio from the variation rate $\Delta V$ % of the lung field area calculated from the front chest image, or a table representing the correspondence relationship between the variation rate $\Delta V$ % of the lung field area calculated from the front chest image and the residual volume ratio or the like. Alternatively, this storage stores the statistical data or scatter plot of the correspondence relationship between the measured values of the residual volume, the functional residual capacity, the total lung capacity and the residual volume ratio measured by the helium closed circuit method, the denitrogenation open circuit method or the body plethysmography, and the lung field area at the maximal inspiratory level (deep inspiratory level) or the variation rate $\Delta V$ % of the lung field area calculated from the front chest image taken by radiation imaging under deep breath, with respect to many subjects.

The operation unit 33 includes a keyboard provided with cursor keys, numeric input keys and various function keys, and a pointing device, such as a mouse, and outputs, to the controller 31, an instruction signal input through a key operation into the keyboard or a mouse operation by a user. The operation unit 33 may include a touch panel on a display screen of the display 34. In this case, the operation unit 33 outputs, to the controller 31, the instruction signal input through the touch panel.

The display 34 may be a monitor, such as an LCD or a CRT, and displays various items according to the instruction of the display signal input from the controller 31.

The communicator 35 includes an LAN adaptor, and a TA or a modem, and controls data transmission and reception to and from each apparatus connected to the communication network NT.

[Operation of Radiographic Image Analysis System 100]

Next, the operation of the radiographic image analysis system 100 in this embodiment is described.

(Operations of Imaging Apparatus 1 and Imaging Console 2)

First, the imaging operations by the imaging apparatus 1 and the imaging console 2 are described.

Figure 2:
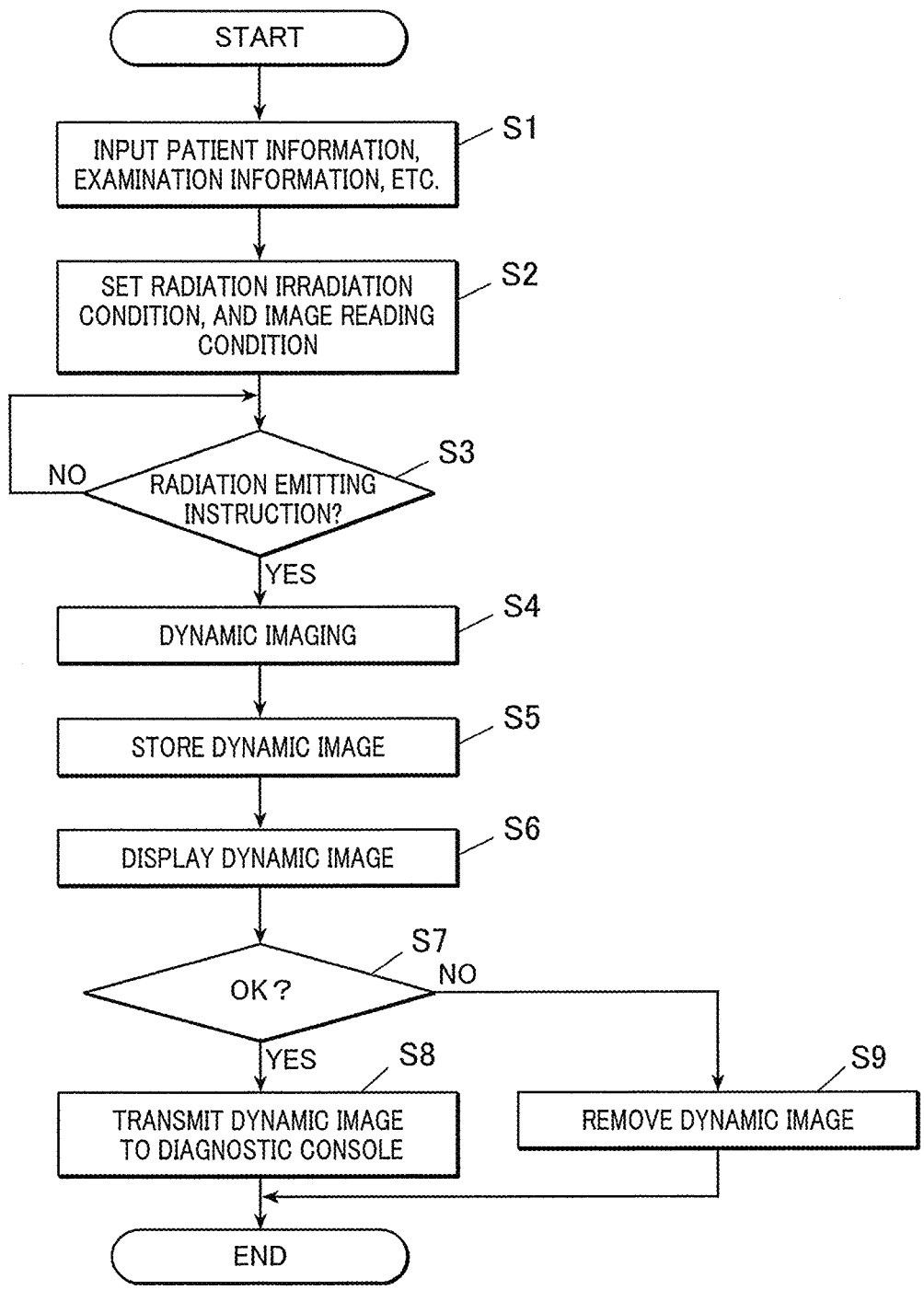
FIG. 2 is a flowchart showing an imaging control process executed by a controller of an imaging console in FIG. 1.

FIG. 2 shows the imaging control process executed by the controller 21 of the imaging console 2. The imaging control process is executed by cooperation between the controller 21 and the program stored in the storage 22.

First, the operation unit 23 of the imaging console 2 is operated by the imaging practitioner, and the patient information on the subject (imaging object M) and the examination information are input (step S1).

Next, the radiation irradiation condition is read from the storage 22 and is set in the radiation emission control apparatus 12, and the image reading condition is read from the storage 22 and is set in the reading control apparatus 14 (step S2).

Next, an instruction of emitting radiation through the operation to the operation unit 23 is waited (step S3). Here, the imaging practitioner positions the imaging object M by disposing this object between the radiation source 11 and the radiation detector 13. Furthermore, an instruction on the respiration state (here, deep breath) is issued to the subject.

When the preparation for imaging is made, the operation unit 23 is operated and a radiation irradiation instruction is input.

When the radiation irradiation instruction is input through the operation unit 23 (step S3; YES), an imaging start instruction is output to the radiation emission control apparatus 12 and the reading control apparatus 14, and the dynamic imaging is started (step S4). That is, the radiation is emitted from the radiation source 11 at a pulse interval set in the radiation emission control apparatus 12, and a frame image is obtained by the radiation detector 13.

After a predetermined number of frames have been taken, an instruction of finishing imaging is output by the controller 21 to the radiation emission control apparatus 12 and the reading control apparatus 14, and the imaging operation is stopped. The number of taken frames is a number allowing at least one respiratory cycle to be imaged. The imaging is performed in a state where no contrast agent is administered to the imaging object M immediately before or during imaging.

The frame images obtained by imaging are sequentially input into the imaging console 2, stored in the storage 22 in association with the respective numbers indicating the imaging order (frame numbers) (step S5), and displayed on the display 24 (step S6). The imaging practitioner verifies positioning and the like with reference to the displayed dynamic image, and determines whether the image suitable for diagnosis is obtained by imaging (imaging OK) or reimaging is required (imaging NG). The operation unit 23 is operated to input a determination result.

When a determination result indicating imaging OK is input by a predetermined operation through the operation unit 23 (step S7; YES), each image of the series of frame images obtained by dynamic imaging is assigned information that includes an identification ID for identifying the dynamic image, the patient information, the examination information, the radiation irradiation condition, the image reading condition, and the number indicating the imaging order (frame number) (written in a header region of the image data in the DICOM format, for example), and is transmitted to the diagnostic console 3 via the communicator 25 (step S8). This process is then finished. On the contrary, a determination result indicating imaging NG is input by a predetermined operation through the operation unit 23 (step S7; NO), the series of frame images stored in the storage 22 is removed (step S9), and this process is finished. In this case, reimaging is required.

[Operation of Diagnostic Console 3]

Next, the operation of the diagnostic console 3 is described.

In the diagnostic console 3, upon receipt of the series of frame images of the dynamic image from the imaging console 2 via the communicator 35, the received dynamic image is stored in the storage 32, and the respiratory function indicator estimation process A shown in FIG. 3 is executed by cooperation between the controller 31 and the program stored in the storage 32.

Here, the inventor of the present application measured the residual volume (RV), the functional residual capacity (FRC) and the total lung capacity (TLC) of each of many subjects by the helium closed circuit method, the denitrogenation open circuit method or the body plethysmography, calculated the lung field area from the front chest image, and discussed the relationship between the lung field area with the residual volume, the functional residual capacity and the total lung capacity.

Figure 4A:
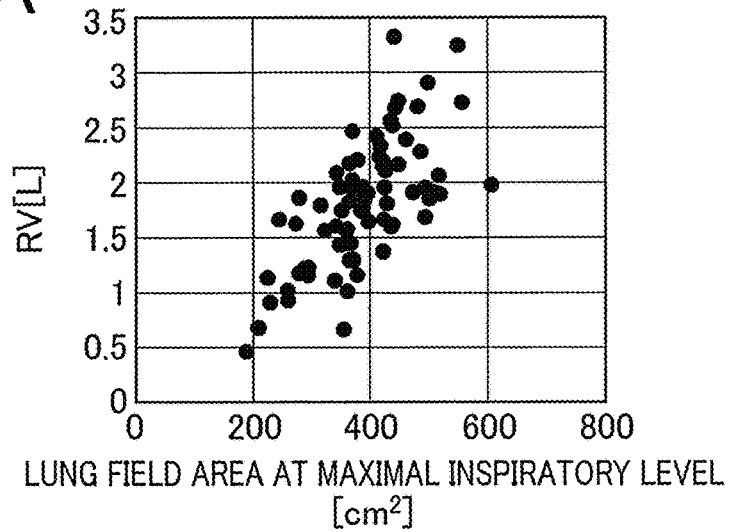
FIG. 4A is a scatter plot showing the relationship between the lung field area and the residual volume at the maximal inspiratory level (deep inspiratory level) in a front chest image taken by radiation imaging under deep breath.
Figure 4B:
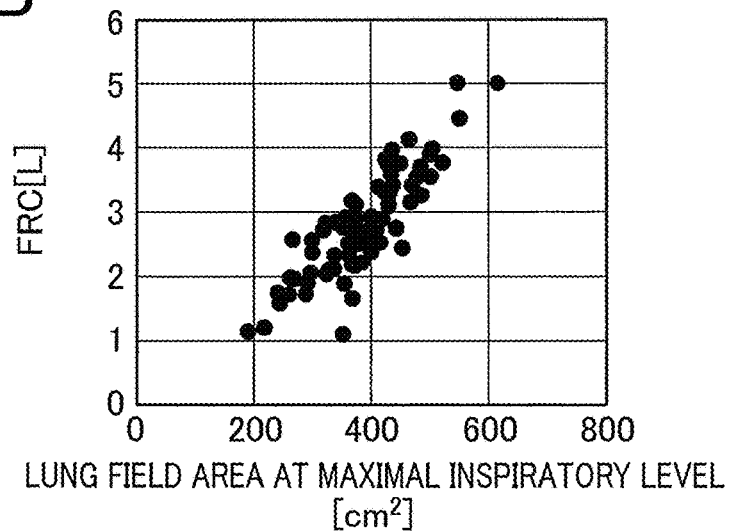
FIG. 4B is a scatter plot showing the relationship between the lung field area and the functional residual capacity at a deep inspiratory level.
Figure 4C:
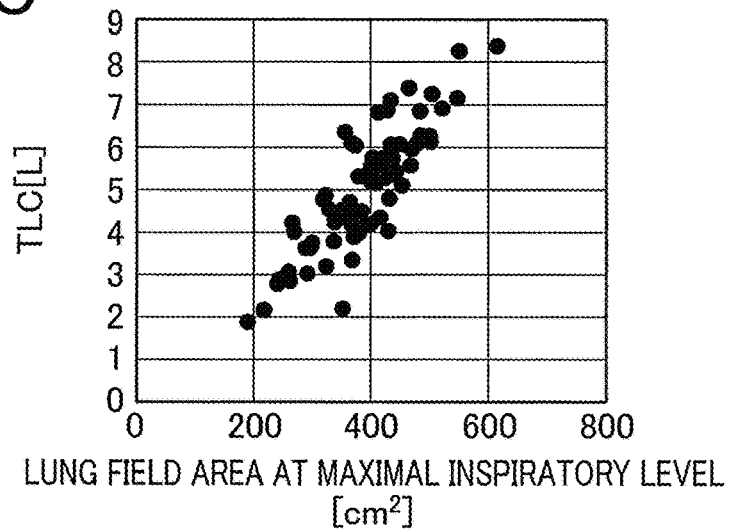
FIG. 4C is a scatter plot showing the relationship between the lung field area and the total lung capacity at the deep inspiratory level.

FIG. 4A is a scatter plot showing the relationship between the lung field area and the residual volume at the maximal inspiratory level (deep inspiratory level) in a front chest image taken by radiation imaging under deep breath. FIG. 4B is a scatter plot showing the relationship between the lung field area and the functional residual capacity at the deep inspiratory level. FIG. 4C is a scatter plot showing the relationship between the lung field area and the total lung capacity at the deep inspiratory level. As shown in FIGS. 4A to 4C, the lung field area has high correlations with the residual volume, the functional residual capacity and the total lung capacity. It has been found out that the residual volume, the functional residual capacity and the total lung capacity can be estimated on the basis of the lung field area.

Likewise, as a result of discussion of the relationship between the variation rate $\Delta V$ % of the lung field area ((the lung field area at the deep inspiratory level–the lung field area at the deep expiratory level)/the lung field area at the deep inspiratory level) and the residual volume ratio, it has been found out that the variation rate $\Delta V$ % of the lung field area is correlated with the residual volume ratio, and the residual volume ratio can be estimated on the basis of the variation rate $\Delta V$ % of the lung field area.

The respiratory function indicator estimation process A is a process of estimating the residual volume, the functional residual capacity, the total lung capacity and the residual volume ratio, from the lung field area.

Hereinafter, referring to FIG. 3, the flow of the respiratory function indicator estimation process A is described.

First, from the received dynamic image, the lung field areas in the frame images at the deep inspiratory level and the deep expiratory level are calculated (step S11).

For example, in step S11, first, the lung field region is extracted from each frame image in the dynamic image. The lung field region is extracted using any of publicly known methods. For example, a threshold is obtained by discrimination analysis, from a histogram of signal values (concentration values) of pixels of the frame image, and a region having a high signal is primarily extracted as a lung field region candidate with reference to the threshold. Next, the edge is detected around the boundary of the primarily extracted lung field region candidate, and points having the maximum edge in small blocks around the boundary are extracted along the boundary, thereby allowing the boundary of the lung field region (regions R encircled by solid lines R in FIG. 5) to be extracted.

Next, the lung field area of each frame image is calculated. For example, the pixel values in the lung field region in each frame image are counted, and are multiplied by the pixel size, thereby allowing the lung field area to be calculated. The maximum area and the minimum area among the lung field areas calculated from the respective frame images are the lung field areas at the deep inspiratory level and at the deep expiratory level, respectively.

Next, the residual volume, the functional residual capacity and the total lung capacity are estimated on the basis of the lung field areas in the frame images at the deep inspiratory level and the deep expiratory level (step S12).

Here, the storage 32 stores a calculation expression of the estimates of the residual volume, the functional residual capacity and the lung capacity, with a variation that is the lung field area in the front chest image at the deep inspiratory level or the deep expiratory level, determined by taking front chest image of each of many subjects at the deep inspiratory level or the deep expiratory level and calculating the lung field area, on the basis of the statistical data obtained by measuring the residual volume, the functional residual capacity and the total lung capacity by the helium closed circuit method, the denitrogenation open circuit method or the body plethysmography, or a table indicating the correspondence relationship between the lung field areas in the front chest images at the deep inspiratory level or the deep expiratory level and the estimates of the residual volume, the functional residual capacity and the lung capacity. In step S12, the residual volume, the functional residual capacity and the total lung capacity are estimated on the basis of the calculation expression or the table stored in the storage 32.

Next, based on the following (Expression 1), the variation rate $\Delta V$ % of the lung field area is calculated (step S13).

$\Delta V$ %=(the lung field area at the deep inspiratory level−lung field area at the deep expiratory level)/lung field area at the deep inspiratory level     (Expression 1)

Next, based on the calculated $\Delta V$ %, the residual volume ratio is estimated (step S14).

Here, the storage 32 stores a calculation expression of the estimate of the residual volume ratio, with a variation that is $\Delta V$ %, determined on the basis of statistical data obtained by taking the front chest images of each of many subjects at the deep inspiratory level and the deep expiratory level, calculating the area variation rate $\Delta V$ % of the lung field on the basis of the lung field area, and calculating the residual volume ratio (the residual volume/total lung capacity) on the basis of the residual volume and the total lung capacity measured by the helium closed circuit method, the denitrogenation open circuit method or the body plethysmography, or a table indicating the correspondence relationship between $\Delta V$ % and the estimate of the residual volume ratio. In step S14, the residual volume ratio is estimated on the basis of the calculation expression or the table stored in the storage 32.

Alternatively, the residual volume ratio may be estimated on the basis of the amount of variation in lung field area in the front chest images at the deep inspiratory level and the deep expiratory level (the lung field area at the deep inspiratory level−the lung field area at the deep expiratory level). Further alternatively, the residual volume ratio may be obtained by dividing the residual volume estimated in step S12 by the total lung capacity.

The estimated results of the residual volume, the functional residual capacity, the lung capacity and the residual volume ratio are displayed on the display 34 (step S15), and the respiratory function indicator estimation process A is finished. Alternatively, a diagram where a perpendicular line is drawn at the positions corresponding to the lung field area calculated in step S11 or the variation rate $\Delta V$ % of the lung field area calculated in step S13 on the scatter plot of the correspondence relationship stored in the storage 32 between each of the measured values of the residual volume, the functional residual capacity, the total lung capacity and the residual volume ratio of many subjects measured by the helium closed circuit method, the denitrogenation open circuit method or the body plethysmography, and the lung field area at the maximal inspiratory level (deep inspiratory level) or the variation rate $\Delta V$ % of the lung field area calculated from the front chest image taken by radiation imaging under deep breath, may be displayed on the display 34, thereby allowing the residual volume, the functional residual capacity, the lung capacity and the residual volume ratio to be estimated from the diagram (also applicable to second to fifth embodiments).

As described above, according to the first embodiment, the residual volume, the functional residual capacity, the total lung capacity and the residual volume ratio can be simply estimated from the chest images.

Second Embodiment

Hereinafter, a second embodiment of the present invention is described.

The configuration of the radiographic image analysis system 100 according to the second embodiment is analogous to that described in the first embodiment with reference to FIG. 1. Consequently, the description is employed. Hereinafter, the operation of the radiographic image analysis system 100 in the second embodiment is described.

Figure 6:
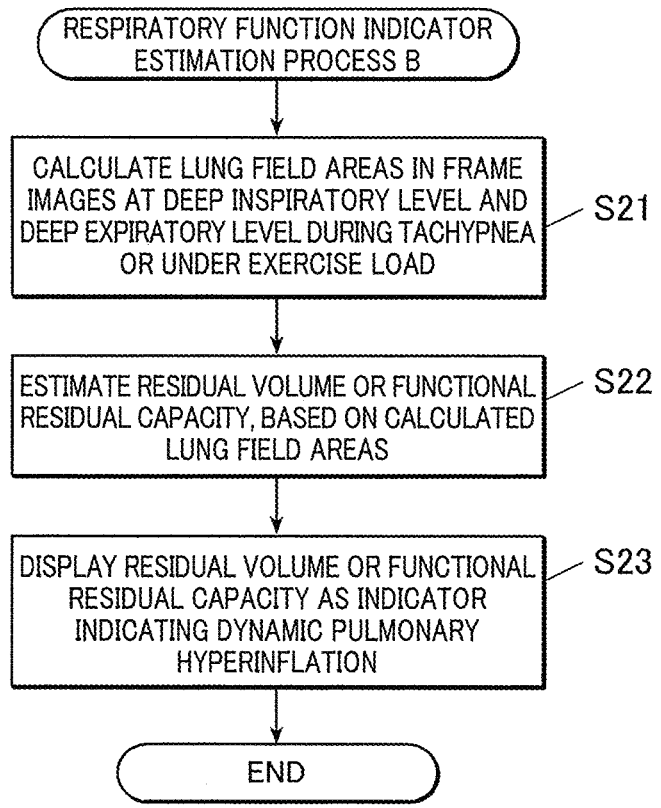
FIG. 6 is a flowchart showing a respiratory function indicator estimation process B executed by a controller of a diagnostic console in FIG. 1 in a second embodiment.

In the second embodiment, images of the imaging object M during tachypnea or under the exercise load are obtained by the imaging apparatus 1 through dynamic imaging. A respiratory function indicator estimation process B shown in FIG. 6 is executed for the obtained dynamic image.

Hereinafter, referring to FIG. 6, the respiratory function indicator estimation process B is described. The respiratory function indicator estimation process B is executed by cooperation between the controller 31 and the program stored in the storage 32.

First, from the received dynamic image of the imaging object M during tachypnea or under the exercise load, the lung field areas in the frame images at the deep inspiratory level and the deep expiratory level are calculated (step S21). The process of step S21 is analogous to that of step S11. Consequently, the description is employed.

Next, the residual volume or the functional residual capacity of the imaging object M is estimated on the basis of the lung field areas in the frame images at the deep inspiratory level and the deep expiratory level (step S22).

Here, as with the first embodiment, the storage 32 stores a calculation expression of the residual volume or the functional residual capacity, with a variation that is the lung field area in the front chest image at the deep inspiratory level or the deep expiratory level, determined by taking front chest image of each of many subjects at the deep inspiratory level or the deep expiratory level and calculating the lung field area, on the basis of the statistical data obtained by measuring the residual volume or the functional residual capacity by the helium closed circuit method, the denitrogenation open circuit method or the body plethysmography, or a table indicating the correspondence relationship between the lung field areas in the front chest images at the deep inspiratory level or the deep expiratory level and the estimates of the residual volume or the functional residual capacity. In step S22, the residual volume or the functional residual capacity is estimated on the basis of the calculation expression or the table stored in the storage 32.

The residual volume or functional residual capacity during tachypnea or under an exercise load are then displayed as an indicator indicating dynamic pulmonary hyperinflation on the display 34 (step S23), and the respiratory function indicator estimation process B finishes.

Early symptoms of COPD include dynamic pulmonary hyperinflation. The dynamic pulmonary hyperinflation is a state where increase in respiration rate due to tachypnea, exercise load or the like prevents air from appropriately being exhaled from the lungs, and makes the lungs inflate too much to prevent air from being inhaled. That is, it is believed that the residual volume or the functional residual capacity of a patient in an early stage of COPD increases during tachypnea or under the exercise load owing to dynamic pulmonary hyperinflation. Accordingly, the respiratory function indicator estimation process B takes a front chest image at the deep inspiratory level or the deep expiratory level during tachypnea or under the exercise load, estimates the residual volume or the functional residual capacity on the basis of the lung field area, and adopts the residual volume or the functional residual capacity as an indicator of dynamic pulmonary hyperinflation. The larger the residual volume or the functional residual capacity is, the higher the possibility of dynamic pulmonary hyperinflation is.

The respiratory function indicator estimation process B shown in FIG. 6 performs dynamic imaging during tachypnea or under the exercise load, estimates the residual volume or the functional residual capacity on the basis of the lung field area calculated from the frame images at the deep inspiratory level and at the deep expiratory level in the obtained dynamic image, and outputs the residual volume or the functional residual capacity as the indicator of the dynamic pulmonary hyperinflation. Alternatively, the process may perform dynamic imaging before and after application of an exercise load (or during a tachypnea process), estimate the residual volume or the functional residual capacity before and after application of the exercise load (or in a tachypnea process), on the basis of the lung field area calculated from the frame images at the deep inspiratory level and at the deep expiratory level among the frame images of each obtained dynamic image, using the calculation expression or the table determined on the basis of the statistical data, and output the variation (the amount of variation or variation rate) as the indicator of the dynamic pulmonary hyperinflation. The larger the variation in residual volume or functional residual capacity is, the higher the possibility of dynamic pulmonary hyperinflation is.

As described above, in the second embodiment, the indicator of the dynamic pulmonary hyperinflation can be easily obtained from the chest images.

Third Embodiment

Figure 5:
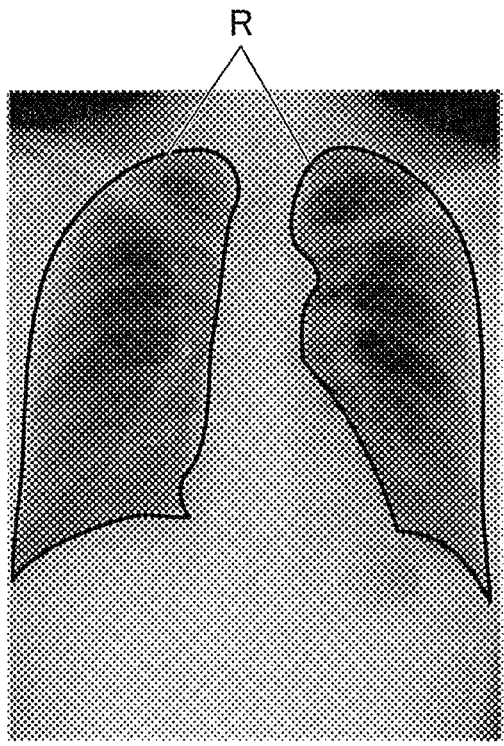
FIG. 5 shows a lung field region extracted in the first embodiment.

It has been described that in step S11 of FIG. 3 in the first embodiment and in step S21 of FIG. 6 in the second embodiment, the regions (regions R) of both the lungs indicated by the solid lines in FIG. 5 are extracted as the lung field regions, and the respiratory function indicators, such as the residual volume, the functional residual capacity, the total lung capacity, the residual volume ratio, and the indicator of the dynamic pulmonary hyperinflation, are estimated on the basis of the lung field area. In COPD, a lesion occurs from the peripheral side (thorax side) in the lung field. Accordingly, it is believed that use of the lung field area only on the peripheral side increases the sensitivity of the respiratory function indicators for COPD, and allows COPD to be identified in an early stage. In a third embodiment, an example of estimating the residual volume, the functional residual capacity, the total lung capacity, the residual volume ratio, and the indicator of the dynamic pulmonary hyperinflation, on the basis of the area of a peripheral part of the lung field, is described.

The configuration and the imaging operation of the radiographic image analysis system 100 in the third embodiment are analogous to those described in the first and second embodiments. Consequently, the description is employed. The flow of the process of calculating each respiratory function indicator in the diagnostic console 3 is substantially analogous to the flows of the first embodiment and the second embodiment. However, the flow is different in that the lung field region is extracted from each frame image of the dynamic image and subsequently the peripheral region of the lung field is extracted and the area thereof is calculated, and in that each respiratory function indicator is estimated on the basis of the area of the peripheral region of the lung field calculated from the frame images at the deep inspiratory level and/or the deep expiratory level. Accordingly, the method of extracting the peripheral region of the lung field, and the method of estimating each respiratory function indicator based on the area of the peripheral region of the lung field are hereinafter described.

Figure 7:
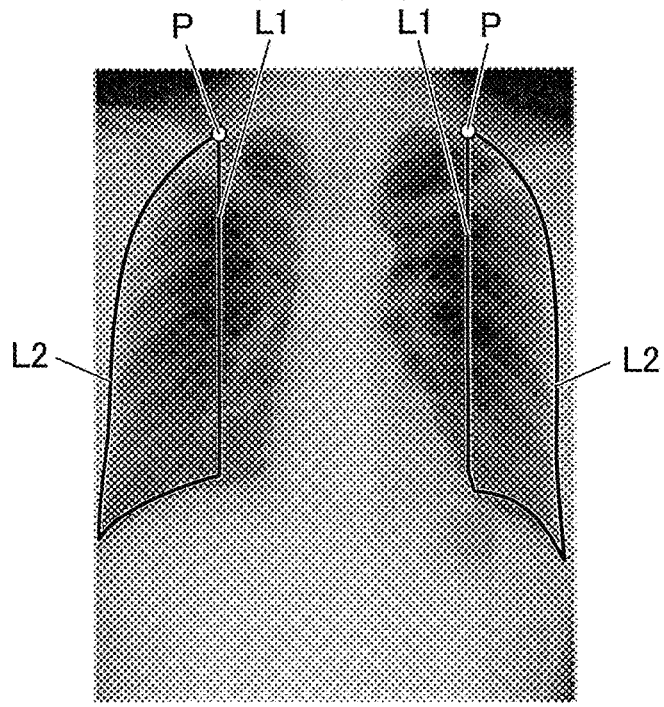
FIG. 7 illustrates a method of extracting a peripheral range of a lung field.

The method of extracting the peripheral region of the lung field, for example, can extract the lung field region from the front chest image (frame image) by the method described in the first embodiment and, as shown in FIG. 7, can extract, as the peripheral region of the lung field, a region (i.e., a part of the lung field near to the thorax) encircled by a perpendicular line L1 from a vertex P of a superiorsulcus and a contour L2 of the lung field near to the thorax, with the perpendicular line L1 being regarded as the boundary between the center side and peripheral side of the lung field. The area of the peripheral region of the lung field can be obtained by counting the pixel values of the extracted peripheral region of the lung field and multiplying the counted values by the pixel size. Alternatively, a horizontal line having endpoints on the contours of the lung field nearer to the center and to the thorax may be drawn at a predetermined position (height) from the diaphragm with respect to each of left and right lungs, and the perpendicular line from the midpoint of the horizontal line may be regarded as the boundary between the central side and the peripheral side of the lung field.

The method of estimating the residual volume, the functional residual capacity, the total lung capacity and the residual volume ratio on the basis of the peripheral area of the lung field may be a method analogous to the method described in the first embodiment.

That is, the calculation expression of the estimates of the residual volume, the functional residual capacity and the total lung capacity that have a variable that is the area of the peripheral side of lung field in the front chest image at the deep inspiratory level or the deep expiratory level and have been determined on the basis of the statistical data, or a table indicating the correspondence relationship between the area of the peripheral side of the lung field in the front chest image at the deep inspiratory level or the deep expiratory level and the estimates of the residual volume, the functional residual capacity and the lung capacity, are preliminarily stored in the storage 32. The controller 31 can estimate the residual volume, the functional residual capacity and the total lung capacity from the area of the peripheral side of the lung field calculated from the frame image at the deep inspiratory level or the deep expiratory level, on the basis of the calculation expression or the table stored in the storage 32.

A calculation expression of the estimate of the residual volume ratio that has a variable that is the area variation rate $\Delta V$ % of the area of the peripheral side of the lung field in the front chest image taken under deep breath, or a table indicating the correspondence relationship between the area variation rate $\Delta V$ % of the area of the peripheral side of the lung field in the front chest image taken under deep breath and the estimate of the residual volume ratio, determined on the basis of the statistical data, is preliminarily stored in the storage 32. The controller 31 can estimate the residual volume ratio from the area variation rate $\Delta V$ % of the area of the peripheral side of the lung field calculated using the frame images at the deep inspiratory level and the deep expiratory level, on the basis of the calculation expression or the table stored in the storage 32.

As described above, in the third embodiment, the residual volume, the functional residual capacity, the lung capacity, the residual volume ratio or the indicator of the dynamic pulmonary hyperinflation is calculated on the basis of the area of the peripheral side of the lung field where a lesion of COPD occurs. Consequently, the residual volume, the functional residual capacity, the lung capacity, the residual volume ratio or the indicator of the dynamic pulmonary hyperinflation that has a high sensitivity to COPD can be obtained.

Fourth Embodiment

In step S11 of FIG. 3 in the first embodiment and step S21 of FIG. 6 in the second embodiment, description has been made where the regions (regions R) of both the lungs indicated by the solid lines in FIG. 5 are extracted as the lung field region, and the residual volume, the functional residual capacity, the total lung capacity, the residual volume ratio, and the indicator of the dynamic pulmonary hyperinflation are estimated on the basis of the lung field area. In general, the expansion and contraction of the lungs are larger at a part nearer to the back (see FIG. 8). Accordingly, in a fourth embodiment, the lung base ends nearer to the back at the deep expiratory level or the deep inspiratory level are estimated from the dynamic image. Based on the lung field area where the estimated lung base end nearer to the back is regarded as the bottom end of the lung field, the residual volume, the functional residual capacity, the total lung capacity, the residual volume ratio and the indicator of the dynamic pulmonary hyperinflation are calculated.

The configuration and the imaging operation of the radiographic image analysis system 100 in the fourth embodiment are analogous to those described in the first and second embodiments. Consequently, the description is employed. The flow of the process of calculating each respiratory function indicator in the diagnostic console 3 is substantially analogous to the flows of the first embodiment and the second embodiment. However, the flow is different in that the lung base ends nearer to the back are estimated from each frame image in the dynamic image, and the lung field area where the estimated lung base ends nearer to the back are regarded as the bottom ends of the lung fields are calculated, and in that each respiratory function indicator is estimated on the basis of the lung field areas where the lung base ends nearer to the back are regarded as the bottom ends of the lung fields, the areas being calculated from the frame images at the deep inspiratory level and/or the deep expiratory level. Accordingly, the method of estimating the positions of the lung base ends nearer to the back from each frame image of the dynamic image, and the method of estimating each respiratory function indicator based on the lung field areas where the lung base ends nearer to the back are regarded as the bottom ends of the lung fields are hereinafter described.

First, the method of estimating the lung base ends nearer to the back, and the method of calculating the lung field areas are described.

Figure 8:
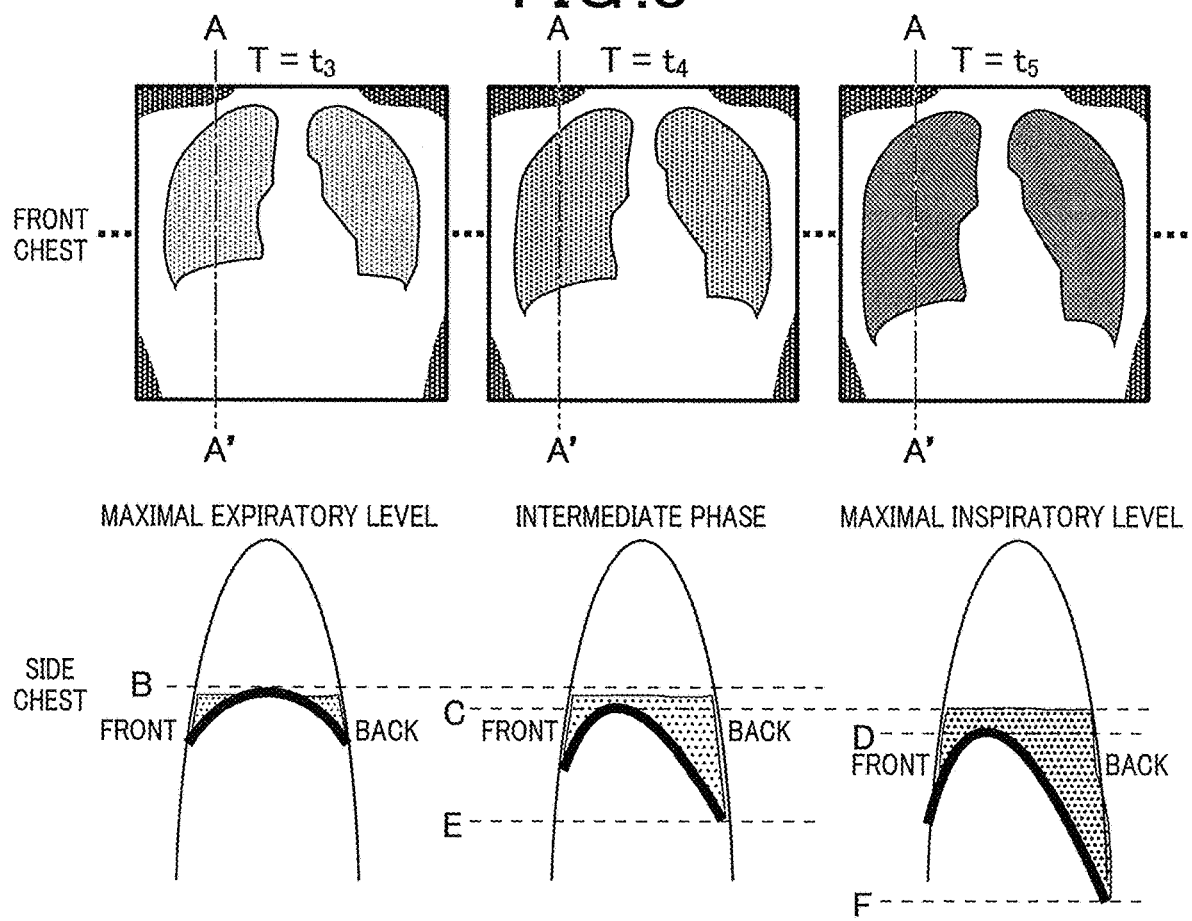
FIG. 8 schematically shows frame images of the front chest (front chest image) and the variation due to respiration on a side at a position indicated by line A-A' in the front chest image.

FIG. 8 schematically shows frame images in the dynamic image of the front chest (front chest image) and the variation due to respiration on a side at a position indicated by line A-A' in the front chest image. FIG. 9A schematically shows the output signal value at the positions indicated by line A-A' in the three front chest images shown in FIG. 8. FIG. 9B schematically shows a difference signal value. In FIGS. 9A and 9B, a line indicated by a broken line indicates the output signal value at the deep expiratory level in FIG. 8. A line indicated by a chain line indicates the output signal value at an intermediate phase and an inter-frame difference value between the intermediate phase and the deep expiratory level in FIG. 8. A line indicated by a solid line indicates the output signal value at the deep inspiratory level and the inter-frame difference value between the deep inspiratory level and the intermediate phase in FIG. 8. In FIG. 9A, between G and B, three lines at the deep expiratory level, the intermediate phase and the deep inspiratory level are substantially overlapped with each other.

The respiratory cycle includes an expiratory period and an inspiratory period. In the expiratory period, the diaphragm rises to discharge air from the lungs, and the regions of the lung fields decrease. At the deep expiratory level, the position of the diaphragm is in a highest state. In the inspiratory period, the diaphragm lowers to thereby inhale air into the lungs, and the regions of the lung fields in the thorax increase. At the deep inspiratory level, the position of the diaphragm is in the most lowered state.

As described above, the lung field region is a region where air enters and is discharged. Consequently, the density of tissue is lower and the amount of radiation transmission is larger than those around the region out of the lung field region. Accordingly, when X-ray imaging is performed, the lung field region has a larger signal value than the region out of the lung field region has.

The position indicated by B in the side view of FIG. 8 is the upper end position of the diaphragm at the maximal expiratory level. The position indicated by C in the side view of FIG. 8 is the upper end position of the diaphragm at the intermediate phase. The position indicated by D in the side view of FIG. 8 is the upper end position of the diaphragm at the maximal inspiratory level. Each of the upper end positions of the diaphragm is the boundary at which the signal value in the lung field region where the density of tissue is low transitions to the signal value in the region out of the lung field region, and can be visually recognized as the lung base position in the front chest image in FIG. 8.

On the other hand, the position indicated by E in the side view of FIG. 8 is the bottom end position of the diaphragm at the intermediate phase. The position indicated by F in the side view of FIG. 8 is the bottom end position of the diaphragm at the maximal inspiratory level. As shown in the side view of FIG. 8, the diaphragm moves largely toward the back in actuality. The lung field resides to the bottom end position of the diaphragm back part. That is, the bottom end position of the diaphragm back part can be estimated as the lung base end nearer to the back. The bottom end position of the diaphragm back part cannot be visually observed. However, the position can be recognized by performing the inter-frame difference process between the adjacent frame images.

When the inter-frame difference process is performed between the adjacent frame images, the upper end position L11 of the diaphragm is the position where the inter-frame difference value is the maximum, as shown in FIG. 9B. The bottom end position L12 of the diaphragm is lower than the upper end position L11, and is the position of the boundary of a region where the inter-frame difference value is substantially zero. The difference value between frame images is calculated by subtracting, from the signal value of the pixel of the n-th frame image, the signal value of the same pixel of the (n−1)-th frame image, for example. For the first frame image, a difference value to be obtained by subtracting the last frame image (for example, the ninth frame in a case of nine frames) from the first frame image is calculated. It is preferred that before application of the inter-frame difference process, a low-pass filter process in the temporal direction be applied to the dynamic image, and temporal variation in signal value due to ventilation be extracted.

The lung base ends nearer to the back is estimated as the bottom end of the lung field, the controller 31 calculates the lung field area with the estimated lung base ends nearer to the back being regarded as the bottom end of the lung field. For example, the side end part of the lung field region connecting the bottom end of the side end part of the lung field region and the lung base ends nearer to the back of the diaphragm extracted in step S11 of FIG. 3 is obtained by interpolation. The region obtained by adding the area of the lung field region extracted in step S11 to the area of the region encircled by the lung field region and the lung base end nearer to the back is calculated as the lung field area. The side end part of the lung field between the lung field region and the lung base end nearer to the back extracted in step S11 may be obtained, for example, by the interpolation process or the like as described above. Alternatively, the lung base end nearer to the back in each frame image may be obtained, and the side end part of the lung field may be estimated from the trajectories of the opposite ends of the obtained base end.

Next, a method of estimating the residual volume, the functional residual capacity, the total lung capacity, the residual volume ratio, and the indicator of the dynamic pulmonary hyperinflation, on the basis of the lung field area, with the lung base end nearer to the back being regarded as the bottom end of the lung field, is described.

The method of estimating the residual volume, the functional residual capacity, the total lung capacity and the residual volume ratio on the basis of the lung field area, with the lung base end nearer to the back being regarded as the bottom end of the lung field, may be a method analogous to the method described in the first embodiment. That is, the calculation expression of the estimates of the residual volume, the functional residual capacity and the total lung capacity that have a variable that is the lung field area, with the lung base end nearer to the back being regarded as the bottom end of the lung field, in the front chest image at the deep inspiratory level or the deep expiratory level and have been determined on the basis of the statistical data, or a table indicating the correspondence relationship between the lung field area, with the lung base end nearer to the back being regarded as the bottom end of the lung field, in the front chest image at the deep inspiratory level or the deep expiratory level and the estimates of the residual volume, the functional residual capacity and the lung capacity, are preliminarily stored in the storage 32. The controller 31 can estimate the residual volume, the functional residual capacity and the total lung capacity from the lung field area, with the lung base end nearer to the back being regarded as the bottom end of the lung field, calculated from the frame image at the deep inspiratory level or the deep expiratory level, on the basis of the calculation expression or the table stored in the storage 32.

A calculation expression of the estimate of the residual volume ratio that has a variable that is the area variation rate $\Delta V$ % of the lung field area, with the lung base end nearer to the back being regarded as the bottom end of the lung field, in the front chest image taken under deep breath, or a table indicating the correspondence relationship between the area variation rate $\Delta V$ % of the lung field area, with the lung base end nearer to the back being regarded as the bottom end of the lung field, in the front chest image taken under deep breath and the estimate of the residual volume ratio, determined on the basis of the statistical data, is preliminarily stored in the storage 32. The controller 31 can estimate the residual volume ratio from the area variation rate $\Delta V$ % of the lung field area, with the lung base end nearer to the back being regarded as the bottom end of the lung field, calculated using the frame images at the deep inspiratory level and the deep expiratory level, on the basis of the calculation expression or the table stored in the storage 32.

As described above, in the fourth embodiment, the residual volume, the functional residual capacity, the lung capacity, the residual volume ratio or the indicator of the dynamic pulmonary hyperinflation is calculated on the basis of the lung field area, with the lung base end nearer to the back being regarded as the bottom end of the lung field. Consequently, the residual volume, the functional residual capacity, the lung capacity, the residual volume ratio or the indicator of the dynamic pulmonary hyperinflation can be more accurately obtained.

Fifth Embodiment

In the aforementioned first to fourth embodiments, the description has been made where the residual volume, the functional residual capacity, the total lung capacity, the residual volume ratio or the indicator of the dynamic pulmonary hyperinflation is estimated on the basis of the area of the lung field regions of the both lungs. Alternatively, the lung field area may be calculated for each lung, and then the residual volume, the functional residual capacity, the total lung capacity, the residual volume ratio or the indicator of the dynamic pulmonary hyperinflation may be calculated for each lung on the basis of the calculated lung field area.

Conventional examinations including spirometry can only obtain information on both the lungs. However, use of the dynamic image can estimate the residual volume, the functional residual capacity, the total lung capacity, the residual volume ratio and the indicator of the dynamic pulmonary hyperinflation, for each lung. Accordingly, the left lung and the right lung can be compared with each other. Furthermore, the residual volume, the functional residual capacity, the total lung capacity, or the indicator of the dynamic pulmonary hyperinflation of a postoperative lung in a case of an operation to one lung can be calculated. Consequently, calculation of the temporal variation of such a value can, in turn, calculate the temporal variation of the lung after the operation.

As described above, the controller 31 of the diagnostic console 3 calculates the lung field area from the chest image obtained by radiation imaging of the chest in one direction, and estimates the residual volume, the functional residual capacity, the total lung capacity or the residual volume ratio of the lung field on the basis of the calculated lung field area.

Consequently, without need of a conventional, expensive and extensive medical instrument, the respiratory function indicators, such as the residual volume, the functional residual capacity and the total lung capacity, can be simply obtained using the chest image.

The description in the above embodiments is preferable examples of the present invention, which is not limited thereto.

For example, in the aforementioned first to the fifth embodiments, the description has been made where the respiratory function indicators such as the residual volume, the functional residual capacity, the total lung capacity, the residual volume ratio or the indicator of the dynamic pulmonary hyperinflation of the lung field are created on the basis of the lung field area at the deep inspiratory level or the deep expiratory level calculated from the chest dynamic image obtained by dynamic imaging of the chest in one direction toward the front chest. Alternatively, the respiratory function indicators, such as the residual volume, the functional residual capacity, the total lung capacity, the residual volume ratio and the indicator of the dynamic pulmonary hyperinflation of the lung field, may be created on the basis of the lung field area at the deep inspiratory level or the deep expiratory level calculated from the chest dynamic image obtained by dynamic imaging of the chest on a chest side. Note that in view of reduction in radiation exposure to a patient, it is preferred to take a front chest image.

For example, in the aforementioned embodiments, the description has been made where the frame image at the deep inspiratory level or the deep expiratory level is identified from the chest dynamic images obtained by dynamic imaging of the chest, and the residual volume, the functional residual capacity, the total lung capacity, the residual volume ratio or the indicator of the dynamic pulmonary hyperinflation of the lung field is created on the basis of the lung field area calculated from the identified frame image. Alternatively, the lung field area may be calculated from the front chest image obtained by still imaging of the front chest at the deep inspiratory level or the deep expiratory level, and the residual volume, the functional residual capacity, the total lung capacity, the residual volume ratio, the indicator of the dynamic pulmonary hyperinflation and the like of the lung field may be created on the basis of the calculated lung field area.

Not all the residual volume, the functional residual capacity, the total lung capacity and the residual volume ratio of the lung field are required to be estimated. For example, only a respiratory function indicator selected by a user may be estimated. The inventor of the present application discussed the relationship between the lung field area at the maximal inspiratory level (deep inspiratory level) in the front chest image taken under deep breath and the vital capacity (VC) measured by a respiratory function examination (spirometry) for each of many subjects, and found out that both were highly correlated. While the residual volume, the functional residual capacity, the total lung capacity and the residual volume ratio of the lung field are estimated on the basis of the lung field area, the vital capacity may be estimated on the basis of the lung field area using an analogous method. Accordingly, the vital capacity can be easily estimated using the chest image. The user can find out the characteristics of an obstructive pulmonary disease and a restrictive pulmonary disease, from the estimates of the residual volume, the functional residual capacity, the total lung capacity, the residual volume ratio and the vital capacity. The estimate of the residual volume may be calculated by subtracting the estimate of the vital capacity calculated on the basis of the lung field area from the estimate of the total lung capacity calculated based on the lung field area.

In the aforementioned embodiments, the description has been made where the estimated respiratory function indicator is displayed on the display 34. However, the output of the respiratory function indicator is not specifically limited. For example, the output may be made by a printer printing on a sheet or be made through audio, or data on the respiratory function indicator may be output to an external apparatus via the communication network NT.

Figure 10A:
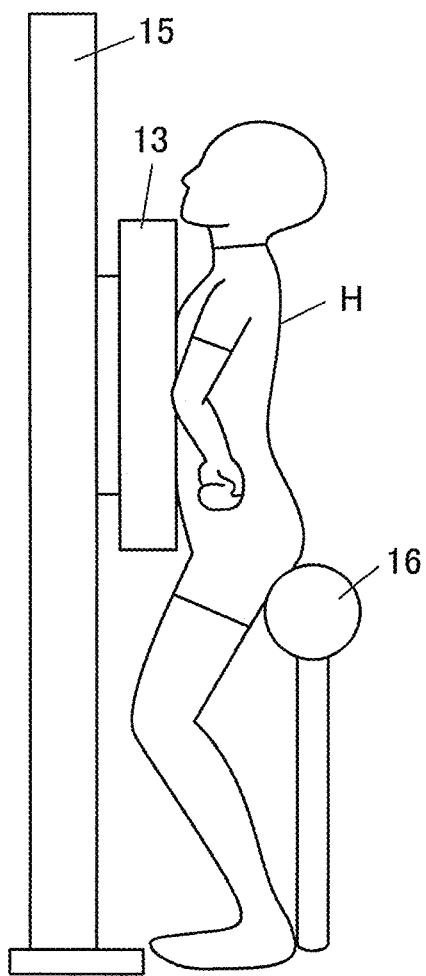
FIG. 10A shows a chair that is provided for an imaging apparatus and allows a subject to sit on the chair's front edge.
Figure 10B:
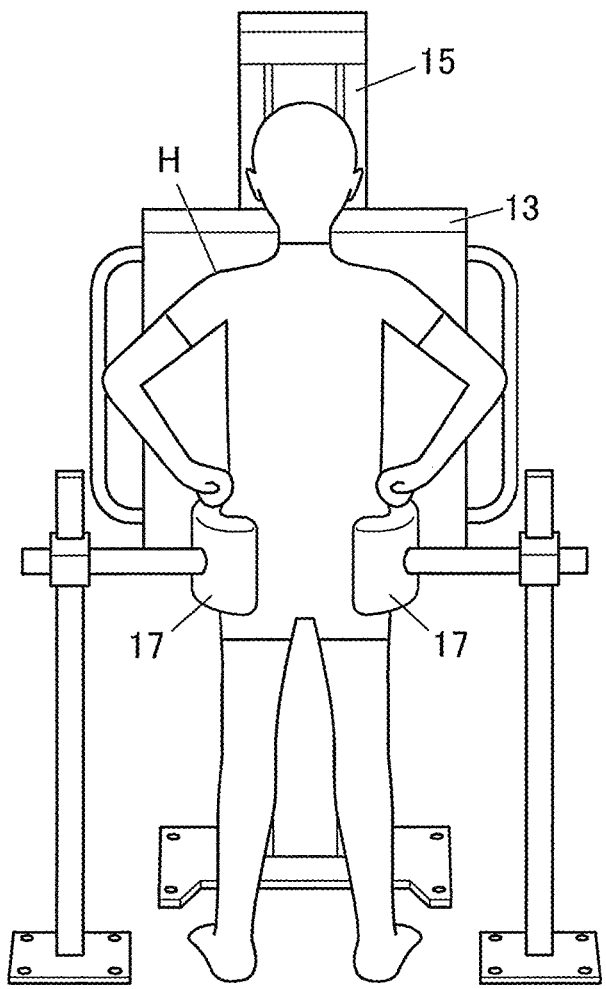
FIG. 10B shows a mechanism that is included in the imaging apparatus and clamps and fixes the pelvis (hips) of the subject at the left and right.
Figure 10C:
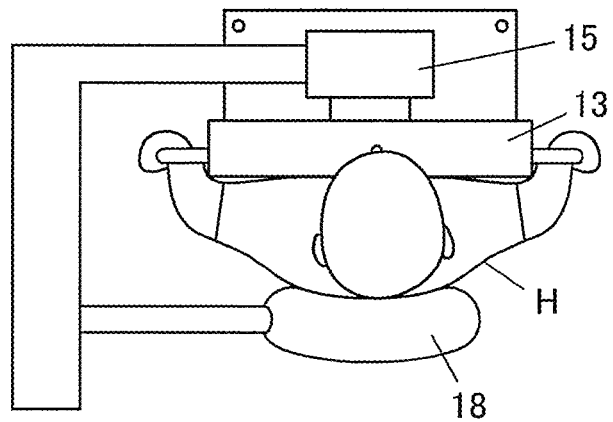
FIG. 10C shows a mechanism that is included in the imaging apparatus and fixes the pelvis (hips) of the subject by pressing from the back to an imaging base.

Particularly, in dynamic imaging, imaging is performed continuously for a long time period (about 20 seconds). Accordingly, to suppress the body motion of the subject during imaging at the upright position, it is preferred that the imaging apparatus 1 be provided with a mechanism of fixing the pelvis (hips). For example, it is preferred that a chair 16 allowing a subject (indicated by H in FIGS. 10A to 10C) to sit on the edge as shown in FIG. 10A, a mechanism 17 clamping and fixing the pelvis (hips) of a subject from the left and right as shown in FIG. 10B, a mechanism 18 pressing and fixing the pelvis (hips) of the subject from the back to the imaging base 15 as shown in FIG. 10C, and the like be provided. If imaging is performed at a completely seated position, the digestive viscera and the diaphragm of the subject rise to prevent deep breath. The chair 16 allowing the subject to sit at the edge is thus provided, which can suppress the body motion of the subject without preventing the subject from respiring. Likewise, the mechanism 17 clamping and fixing the pelvis (hips) from the left and right, and the mechanism 18 pressing and fixing the pelvis (hips) from the back to the imaging base 15 can suppress the body motion of the subject without preventing the respiration and the motion of the thorax of the subject. In the case where the mechanism 18 presses and fixes the pelvis (hips) from the back to the imaging base 15, it is preferred that a mechanism, not shown, ventrally fixing the subject be also provided at the same time, and the hips of the subject be clamped and fixed from the front and back so as to prevent the hips of the subject from moving during imaging. These mechanisms can prevent the body of the subject from moving during dynamic imaging for about 20 seconds. In particular, in a case where the amount of variation in the signal value in the lung field is quantified or visualized, the amount of variation in the signal value caused by body motion, which is to be a noise component, can be suppressed.

The controller 31 of the diagnostic console 3 may quantify and visualize the relationship between the motions of structures in the lung field and the motion of the diaphragm in the chest dynamic images. For example, a method, such as template matching, is applied to a local region including the diaphragm in a certain frame image and multiple local regions in the lung field where the diaphragm is not included, to obtain the position of a corresponding region in a frame image temporarily apart from by multiple frames, and the amount of movement and the movement direction with respect to each local region are calculated. For each local region, by displaying with the calculated amount of movement being overlaid as a numerical value on the chest dynamic image, or by displaying an arrow having the length corresponding to the amount of movement and the direction corresponding to the movement direction so as to be overlaid on the chest dynamic image or by displaying a color image where each local region in the lung field is mapped with a color having a chroma corresponding to the amount of movement and a hue corresponding to the movement direction so as to be overlapped on the chest dynamic image, the relationship between the motions of structures in the lung field and the motion of the diaphragm in the chest dynamic images can be quantified and visualized. Accordingly, the user can easily recognize a site having inactive movement in the lung field with respect to the diaphragm. The recognition can be utilized to identify a clinical state. For example, in a case where the diaphragm moves but pulmonary vessels do not move, it can be identified that the inside of the lungs does not move and gas is not exchanged. The amount of movement and the movement direction described above may have values with reference to the amount of movement and the movement direction of the local region including the diaphragm. For example, the amount of movement and the movement direction of each local region in the lung field that does not include the diaphragm may respectively be a value obtained by dividing this amount by the amount of movement of the local region including the diaphragm, and a degree deviating from the movement direction of the local region including the diaphragm. Accordingly, the motions of structures in the lung field with reference to the motion of the diaphragm can be calculated as quantitative values. The user can more easily grasp the relationship of the motions of structures in the lung field with reference to the motion of the diaphragm.

Before the position of the corresponding region in the frame image temporally apart by multiple frames is obtained using a method, such as template matching, a frame image where the intensities of costal shades are reduced may be generated for each frame image using a publicly known method, and the position of the corresponding region in the frame image temporally apart by multiple frames from the generated frame image may be calculated. Typically, in a chest dynamic image under respiration, the costae and pulmonary vessels move in the opposite directions. Accordingly, such reduction in the intensities of the costal shades can more accurately quantify the relationship between the motions of the pulmonary vessels in the lung field and the motion of the diaphragm in the chest dynamic image.

The description has been made that the relationship between the motions of structures in the lung field and the motion of the diaphragm in the chest dynamic image is quantified and visualized. However, the relationship between the motions of structures in the lung field and the motion of the heart may be quantified and visualized by an analogous method. As with the motion of the diaphragm, the user can easily recognize a site having inactive movement in the lung field with respect to the motion of the heart accordingly. The recognition can be utilized to identify a clinical state.

The lung field of a patient having a disease, such as pneumonia or pulmonary fibrosis, has a small X-ray transmission amount. Accordingly, the signal value decreases in an X-ray image in comparison with the lung field of a healthy subject, and is displayed to be whitish (with a low concentration). If the lung field is displayed to be whitish, the amount of variation in signal value in the lung field increases even though the amount of motion of the diaphragm is the same. Consequently, the dynamic image, or the visualized image where the color corresponding to the quantitative value (numerical value) of the amount of variation in local signal value, or the amount of variation in the signal value in the lung field is overlaid on the dynamic image looks well (healthy) in the motion of the lung field. Accordingly, it is preferred that the controller 31 of the diagnostic console 3 correct the amount of variation in signal value on the basis of the lung field concentration (signal value) in each frame image of the dynamic image. To calculate the amount of variation in the signal value in the lung field, for example, a calculation expression indicating the relationship between the characteristic amount obtained from the signal value in the lung field (e.g., an average signal value in the lung field) and a correction coefficient, a table indicating the correspondence relationship between the characteristic amount obtained from the signal value in the lung field and the correction coefficient or the like is stored in the storage 32, the characteristic amount obtained from the signal value in the lung field in the frame image that is a target of calculation of the amount of variation in the signal value in the dynamic image is calculated, the correction coefficient corresponding to the characteristic amount is obtained on the basis of the calculation expression or the table stored in the storage 32, and the calculated amount of variation in the signal value in the lung field is multiplied by the obtained correction coefficient, thereby allowing the corrected amount of variation in the signal value in the lung field to be obtained. Accordingly, even in a case where a patient has a disease, such as pneumonia or pulmonary fibrosis, and the lung field is displayed to be whitish, increase in the amount of variation in signal value can be suppressed. The user can more appropriately grasp the motion state in the lung field on the basis of the amount of variation in signal value. Preferably, the controller 31 of the diagnostic console 3 receives the radiation irradiation condition from the imaging apparatus 1, and the characteristic amount obtained from the signal value in the lung field is calculated on the basis of the received radiation irradiation condition, and body shape information, such as the height and the weight, on the patient stored in the storage 32. The signal value in the lung field depends on the height and weight of the patient and the radiation irradiation condition. For example, even if the radiation irradiation condition is the same, a patient with a large body shape has a small X-ray transmission amount, and the signal value in the lung field decreases. Accordingly, the amount of variation in signal value in the lung field can be more accurately corrected by multiplication by a coefficient according to the size of the body shape of the patient to adjust the value of the characteristic amount obtained from the signal value in the lung field.

To display multiple chest images (dynamic image) taken at different times, the controller 31 may adjust the position so that a predetermined site of the chest (e.g., superiorsulcus, hilus, the same cervical spines, etc.) can be at the same position (height), and display the images in parallel on the display 34. Consequently, multiple chest images can be easily compared with each other, and variation at different times can be easily grasped.

Figure 11A:
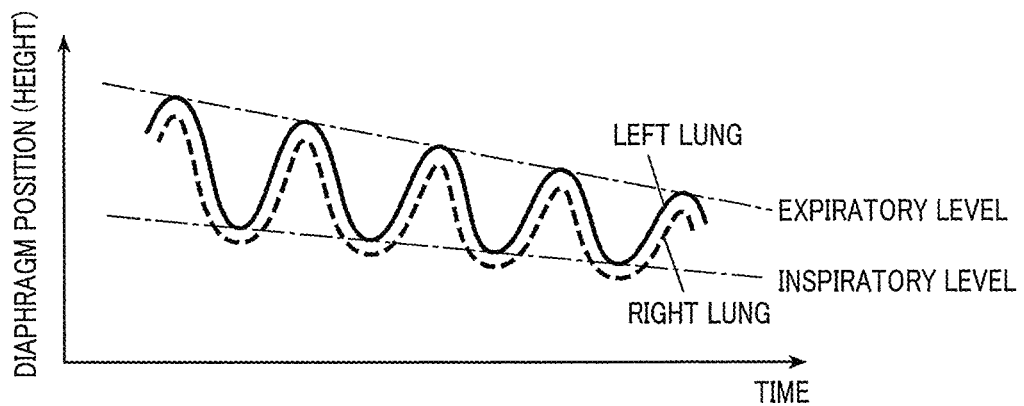
FIG. 11A is a graph of temporal variation in the position of the diaphragm between the left and right lungs calculated from chest images of a subject having an obstructive pulmonary disease taken under an exercise load or in a tachypnea process.
Figure 11B:
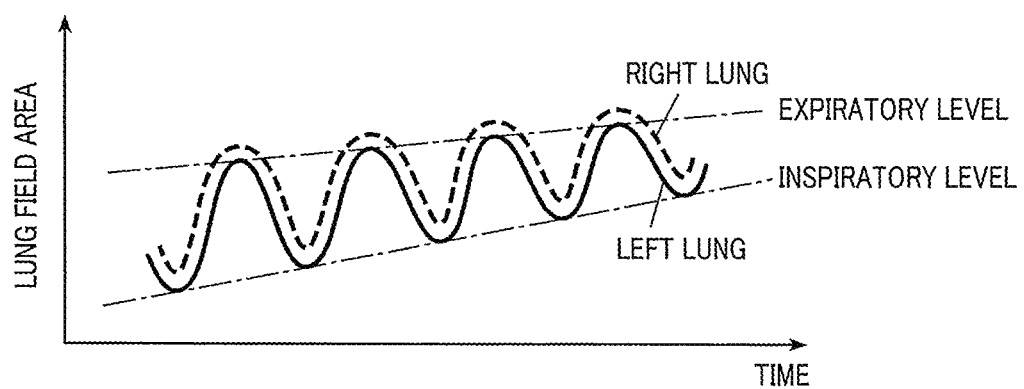
FIG. 11B is a graph of temporal variation in the lung field area of the left and right lungs calculated from chest images of a subject having an obstructive pulmonary disease taken under the exercise load or in the tachypnea process.

For each frame image of chest images taken under the exercise load or in a tachypnea process, the position (height) of the diaphragm may be calculated by a method, such as edge recognition, with respect to each of the left and right lungs, or the lung field contour may be detected by the method described above, the lung field area may be calculated, and the calculated position of the diaphragm at the left and right lungs or the temporal variation in lung field area may be displayed, as the indicator indicating the state of dynamic pulmonary hyperinflation, on the display 34 in a form of a graph. As shown in FIGS. 11A and 11B, in the subject of an obstructive pulmonary disease, such as COPD, the position of the diaphragm is lowered and the lung field area is increased under the exercise load or in a tachypnea process as the time elapses, the amount of movement of the diaphragm position or the amount of variation of the lung field area between the inspiratory level and the expiratory level decreases. Consequently, the user can grasp the degree of dynamic pulmonary hyperinflation, on the basis of the displayed graph of the diaphragm position or the temporal variation in lung field area. Furthermore, from the diaphragm position at the left and right lungs or the temporal variation of the lung field area, the temporal transition of the diaphragm position or the lung field area at the expiratory level may be calculated, and the quantitative value indicating the degree of the increase and decrease may be calculated as the indicator indicating the state of the dynamic pulmonary hyperinflation. For example, the parameter of an approximate expression where the temporal transition of the calculated lung field area at the expiratory level is linearly approximated or curve-approximated (for example, a slope in the case of linear approximation) is calculated and displayed as an indicator indicating dynamic pulmonary hyperinflation. In a case where the degree of dynamic pulmonary hyperinflation is high, for example, the slope in the case where the temporal transition of the lung field area at the expiratory level is linearly approximated is large. Consequently, the user can more simply grasp the degree of dynamic pulmonary hyperinflation of the subject by verifying this quantitative value. Furthermore, in the front chest image taken as a still image at the maximal inspiratory level or the frame image at the maximal inspiratory level in the dynamic image of the front chest, the diaphragm position at the left and right lungs or the lung field area may be calculated. The difference between the calculated diaphragm position at the left and right lungs or lung field area at the maximal inspiratory level and the diaphragm position at the left and right lungs or the lung field area calculated from each frame image of the dynamic image of the front chest taken under the exercise load or in the tachypnea process may be calculated, and the temporal variation in the calculated difference value may be displayed on the display 34 in a form of a graph. Accordingly, the temporal variation in the respiratory function indicator corresponding to the maximal inspiratory capacity (IC) is displayed, which facilitates the user to grasp the subject's exercise tolerance and degree of respiratory distress under exertion by verifying the temporal variation. Here, as described in the fourth embodiment, to calculate the lung field area, the lung base end nearer to the back may be estimated from each frame image in the dynamic image, and the lung field area, with the estimated lung base end nearer to the back being regarded as the bottom end of the lung field, may be calculated. Accordingly, based on the motion of the part nearer to the back where the expansion and contraction during respiration are large, the indicator of the dynamic pulmonary hyperinflation can be more accurately obtained. In a case of imaging in a tachypnea process, it is preferred that the imaging apparatus 1 have a respiration guidance mechanism of instructing the subject in the inspiratory timing and expiratory timing through audio or display on a monitor screen.

For example, the above description discloses an example using the hard disk, the semiconductor nonvolatile memory or the like as a computer-readable medium for the program according to the present invention. However, the scope is not limited to this example. A portable recording medium, such as CD-ROM, may be adopted as another computer-readable medium. A medium for providing data of the program according to the present invention via a communication line may be carrier waves.

Alternatively, the detailed configuration and detailed operation of each of apparatuses constituting the radiographic image analysis system may also be appropriately modified in a scope without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of the description, claims, drawings and abstract of Japanese Patent Application No. 2018-084693, filed on Apr. 26, 2018 with Japan Patent Office, is incorporated herein by reference in its entirety.

What is claimed is:

1. A radiographic image analysis apparatus, comprising: a hardware processor that:
calculates an area of a lung field from a chest image obtained by dynamic imaging in which radiation is emitted to a chest of a subject, and
estimates at least one of a residual volume, a functional residual capacity, a total lung capacity and a residual volume ratio of the lung field, based on the calculated lung field area of the subject and a calculation expression or a table that are determined based on statistical data obtained from multiple subjects other than the subject, wherein the statistical data indicates a relationship between (i) said at least one of the residual volume, the functional residual capacity, the total lung capacity, and the residual volume ratio and (ii) the lung field area.

2. The radiographic image analysis apparatus according to claim 1,
wherein the chest image is a front chest image, and
the hardware processor estimates said at least one of the residual volume, the functional residual capacity, the total lung capacity and the residual volume ratio of the lung field, based on a part of an area nearer to a thorax in the calculated area of the lung field.

3. The radiographic image analysis apparatus according to claim 1,
wherein the chest image is a front chest image, and
the hardware processor estimates a lung base end nearer to a back in the lung field from the front chest image, calculates a lung field area, with the lung base end nearer to the back being regarded as a bottom end of the lung field, and estimates said at least one of the residual volume, the functional residual capacity, the total lung capacity and the residual volume ratio of the lung field, based on the calculated lung field area, with the lung base end nearer to the back being regarded as the bottom end of the lung field.

4. The radiographic image analysis apparatus according to claim 1, wherein:
the chest image is a front chest image, and
the hardware processor calculates an area of the lung field with respect to each lung, and estimates said at least one of the residual volume, the functional residual capacity, the total lung capacity and the residual volume ratio with respect to each lung, based on the calculated lung field area with respect to each lung.

5. The radiographic image analysis apparatus according to claim 1,
wherein the chest image is a chest image taken during tachypnea or under an exercise load, and
the hardware processor estimates, as an indicator of dynamic pulmonary hyperinflation, the residual volume or the functional residual capacity of the lung field estimated based on the area of the lung field calculated from the chest image taken during the tachypnea or under the exercise load.

6. The radiographic image analysis apparatus according to claim 1,
wherein the hardware processor calculates the area of the lung field from the chest image taken before or after application of an exercise load or during a tachypnea process, estimates the residual volume or the functional residual capacity before or after application of the exercise load or during the tachypnea process, based on the area of the lung field calculated from the chest image taken before or after application of the exercise load or during the tachypnea process, and estimates variation in the estimated residual volume or the functional residual capacity before or after application of the exercise load or during the tachypnea process, as an indicator of dynamic pulmonary hyperinflation.

7. A radiographic image analysis system, comprising:
a radiographic imaging apparatus that performs radiation imaging of a chest, and obtains a chest image; and
the radiographic image analysis apparatus according to claim 1.

8. The radiographic image analysis apparatus according to claim 1,
wherein the statistical data includes data on a relationship between lung field areas obtained by dynamic imaging of the multiple subjects and at least one of residual volumes, functional residual capacities, and total lung capacities obtained by a method other than the dynamic imaging of the multiple subjects.

9. The radiographic image analysis apparatus according to claim 8,
wherein the method other than the dynamic imaging is a helium closed circuit method, a denitrogenation open circuit method, or a body plethysmography.

10. The radiographic image analysis apparatus according to claim 1,
wherein the statistical data includes data on a relationship between variation rates of lung field areas obtained by dynamic imaging of the multiple subjects and residual volume ratios obtained by a method other than the dynamic imaging.

11. The radiographic image analysis apparatus according to claim 10,
wherein the method other than the dynamic imaging is a helium closed circuit method, a denitrogenation open circuit method or a body plethysmography.

12. The radiographic image analysis apparatus according to claim 1,
wherein the hardware processor calculates the lung field area based on a frame image at a deep inspiratory level or a frame image at a deep expiratory level among multiple frame images of the dynamic image.

13. The radiographic image analysis apparatus according to claim 1,
wherein the lung field area calculated by the hardware processor is an area of a part nearer to a thorax of the chest.

14. A non-transitory computer-readable storage medium having stored thereon a program for analysis concerning a dynamic image obtained by dynamic imaging in which radiation is emitted to a chest of a subject, the program being executable by a computer to control the computer to perform functions comprising:
calculating an area of a lung field from a chest image obtained by the dynamic imaging in which radiation is emitted to the chest of the subject; and
estimating at least one of a residual volume, a functional residual capacity, a total lung capacity and a residual volume ratio of the lung field, based on the calculated lung field area of the subject and a calculation expression or a table that are determined based on statistical data obtained from multiple subjects other than the subject, wherein the statistical data indicates a relationship between (i) said at least one of the residual volume, the functional residual capacity, the total lung capacity, and the residual volume ratio and (ii) the lung field area.

15. The storage medium storing the program of analysis according to claim 14,
wherein the statistical data includes data on a relationship between lung field areas obtained by dynamic imaging of the multiple subjects and at least one of residual volumes, functional residual capacities, and total lung capacities obtained by a method other than the dynamic imaging of the multiple subjects.

16. The storage medium storing the program of analysis according to claim 14,
wherein the statistical data includes data on a relationship between variation rates of lung field areas obtained by dynamic imaging of the multiple subjects and residual volume ratios obtained by a method other than the dynamic imaging.

17. A radiographic image analysis method for analysis concerning a dynamic image obtained by dynamic imaging in which radiation is emitted to a chest of a subject, the method comprising:
calculating, by a hardware processor, an area of a lung field from a chest image obtained by the dynamic imaging in which radiation is emitted to the chest of the subject; and
estimating, by the hardware processor, at least one of a residual volume, a functional residual capacity, a total lung capacity and a residual volume ratio of the lung field, based on the calculated lung field area of the subject and a calculation expression or a table that are determined based on statistical data obtained from multiple subjects other than the subject, wherein the statistical data indicates a relationship between (i) said at least one of the residual volume, the functional residual capacity, the total lung capacity, and the residual volume ratio and (ii) the lung field area.

18. The radiographic image analysis method according to claim 17,
wherein the statistical data includes data on a relationship between lung field areas obtained by dynamic imaging of the multiple subjects and at least one of residual volumes, functional residual capacities, and total lung capacities obtained by a method other than the dynamic imaging of the multiple subjects.

19. The radiographic image analysis method according to claim 17,
wherein the statistical data includes data on a relationship between variation rates of lung field areas obtained by dynamic imaging of the multiple subjects and residual volume ratios obtained by a method other than the dynamic imaging.

* * * * *